United States Patent [19]

Suzuki

[11] 4,324,797

[45] Apr. 13, 1982

[54] METAL SOAP COMPOSITIONS

[75] Inventor: Hiroshi Suzuki, Ibaraki, Japan

[73] Assignee: Seiichi Ishizaka, Director General of Agency of Industrial Science and Technology, Tokyo, Japan

[21] Appl. No.: 173,819

[22] Filed: Jul. 30, 1980

[30] Foreign Application Priority Data

Aug. 8, 1979 [JP] Japan ..................... 54-100919

[51] Int. Cl.$^3$ ..................... A61K 31/28; A61L 13/00; B01F 17/00; C09K 15/32

[52] U.S. Cl. ..................... 424/287; 252/89.1; 252/133; 252/356; 252/363.5; 252/389 R; 252/DIG. 11; 424/288; 424/289; 424/294; 424/295; 424/315; 424/318; 424/319

[58] Field of Search ............... 252/107, 108, 109, 117, 252/130, 131, 132, 133, 135, 546, 154, 155, 89.1, 363.5, DIG. 11, 356, 389 R; 424/287, 288, 289, 294, 295, 318, 319, 315

[56] References Cited

U.S. PATENT DOCUMENTS

| | | | |
|---|---|---|---|
| 2,920,045 | 1/1960 | Hearn | 252/548 |
| 3,454,500 | 7/1969 | Lancashire | 252/110 |
| 3,775,052 | 11/1973 | Van Paassen | 8/137 |
| 3,976,588 | 8/1976 | McLaughlin | 252/117 |
| 4,000,082 | 12/1976 | Otrhalek | 252/135 |
| 4,240,919 | 12/1980 | Chapman | 252/95 |

FOREIGN PATENT DOCUMENTS

| | | |
|---|---|---|
| 46-20461 | 2/1971 | Japan . |
| 50-04407 | 6/1975 | Japan . |

*Primary Examiner*—Dennis L. Albrecht

*Attorney, Agent, or Firm*—Birch, Stewart, Kolasch & Birch

[57] ABSTRACT

The water-soluble metal soap compositions are provided comprising essentially a metal soap expressed by the general formula (RCOO)xM (Wherein M represents lithium or a non-alkali metal atom, x represents its valency and R represents a hydrocarbon radical having 4 to 20 carbon atoms) and a chelating agent such as polybasic carboxylic acids, polyaminocarboxylic acid salts, etc., the metal soap being contained therein in an amount in the range of 10 to 1/1000 part by weight based on one part of the chelating agent. The aqueous solutions of the metal soap compositions exhibit such a behavior as if they were a single surfactant, and also exhibit excellent surface active properties which are similar or superior to those of conventional surfactants. Further, addition of conventional surfactants to the compositions can notably enhance the performances of the chelating agent such as chelate effect and metal soap-solubilizing effect.

6 Claims, No Drawings

METAL SOAP COMPOSITIONS

BACKGROUND OF THE INVENTION

1. Field of the Invention

This invention relates to metal soap compositions comprising essentially a metal soap and a chelating agent, which can easily be made up into a transparent aqueous solution.

2. Description of the Prior Art

Heretofore, any of metal soap have been scarcely soluble in water and soluble only in special oils. Thus, their application fields have been restricted to lubricants, stabilizers, water-proop agents, etc. in non-aqueous substance such as oils, synthetic resins, etc., and almost all of them have been used in the form of powder or oil solution.

On the other hand, fatty acid soaps react with calcium ion, iron ion or the like in hard water to form metal soaps which often precipitate to thereby reduce their surface active properties including washing effect; hence metal soap thus formed are avoided as scum. Accordingly, chelating agents have been usually blended into detergents, in advance, to thereby prevent formation of metal soaps.

Further, even when metal soaps are soluble in solvents, such metal soaps have a substantially low solubility and those which are soluble at low temperatures are few. For example, barium stearate is scarcely soluble in all solvents, and when added to water, it floats up like pollen, and even when it is heated under shaking for a long time, barium stearate does not mix with water at all. Further, metal soaps have a tendency that they are hydrolyzed in contact with water, and some of them are hydrolyzed even by a slight amount of water.

The inventor of this invention previously made various studies to develop the uses of metal soaps having drawbacks in respect to solubility and stability and thus having been restricted in application fields and also to elevate the performances of conventional surfactants still more. As a result, the inventor of this invention proposed a surfactant composition obtained by dissolving a metal soap in a water-soluble surfactant in a definite proportion or admixing the both in advance in a proportion in which the both are soluble in water (Japanese patent publication No. 20461/1972). Since the metal soaps in the compositions are solubilized by the effect of surfactants, the compositions exhibit various superior surface active properties by the combination of the properties of the both. On the other hand, however, such a composition requires surfactants in a relatively large proportion; hence the properties of the resulting composition are controlled considerably by the properties of surfactants. In this respect, such a composition has not always been satisfactory.

Thus, the inventor of this invention has further made strenuous studies in order to overcome the above-mentioned drawback, and as a result has found that when a chelating agent is added to a metal soap in a definite proportion, it is possible to effect solubilization of the metal soap in water, and yet no hydrolysis occurs; and the metal soap composition behaves as if it is a single surfactant and yet exhibits various superior surface active properties. The present invention has been made based on this finding.

SUMMARY OF THE INVENTION

An object of the present invention is to provide a metal soap composition which dissolves easily in water to form a transparent aqueous solution.

Another object of the present invention is to provide a metal soap composition which exhibits a superior stability in its dissolved state in water.

A further object of the present invention is to provide a novel metal soap composition which comprises a combination of a metal soap with a chelating agent and behaves as if it is a single surfactant.

A still further object of the present invention is to provide a novel metal soap composition which comprises a metal soap, a chelating agent and a surfactant added to the former two, and which is soluble in water and yet has a superior stability therein.

Other and further objects, features and advantages of the present invention will be more fully apparent from the description mentioned below.

The present invention resides in:

Water soluble metal soap compositions comprising essentially a metal soap represented by the general formula $(RCOO)xM$ (Wherein M represents a metal atom selected from the group consisting of lithium and non-alkali metals, x represents the valency of said metal and R represents a hydrocarbon radical having 4 to 20 carbon atoms), and a chelating agent said metal soap being contained in said compositions in an amount in the range of 10 to 1/1000 part by weight based on one part of said chelating agent.

The present invention resides further in metal soap compositions obtained by further adding a surfactant to the afore-said metal soap compositions in a definite amount.

DESCRIPTION OF THE PREFERRED EMBODIMENTS

Metal soaps used in the metal soap compositions of the present invention refer to known metal salts of saturated, unsaturated hydroxy, straight chain or branched chain fatty acids, naphthenic acids, rosin acids or the like, and as for the above-mentioned metal, there are enumerated metals of I to VIII groups of the Periodic Table, i.e. Ia group (Li), IIa group (Mg, Ca, Ba, etc.), IIIa group (B, Al, etc.), IVa group (Si, Sn, Pb, etc.). Va group (As, Sb, Bi), Ib group (Cu, Ag, etc.), IIb group (Zn, etc.), IVb group (Ti, Zr, etc.), Vb group (V, etc.), VIb group (Cr, Mo, W), VII group (Mn, etc.) and VIII group (Fe, Co, Ni, etc.).

Examples of the metal soaps are lithium stearate, calcium ricinoleate, lithium laurate, cobalt laurate, magnesium laurate, alminium monooleate, stannous caprate, copper naphthenate, zinc linoleate, zirconium rosinate, vanadium caprylate, tungsten capronate, manganese ricinoleate, cobalt myristate, calcium salt of castor oil fatty acid, magnesium salt of castor oil fatty acid, trialuminium octoate, etc.

Further, as for the chelating agent used in the present invention, (1) polybasic carboxylic acids and salts thereof, (2) oxymonocarboxylic acids and alkali metal (other than lithium) salts thereof, (3) imidosulfates, (4) polyphosphates, (5) amines, (6) amino acids and salts thereof, (7) polyaminocarboxylic acid salts, (8) sulfur-containg carboxylic acid salts, etc. are enumerated.

Polybasic carboxylic acids and salts thereof of the above-mentioned item (1) include dibasic to hexabasic acids of chain form and ring form. As for their specific examples, dibasic carboxylic acids such as malonic acid, tartaric acid, malic acid, maleic acid, fumaric acid, oxadipropionic acid, and tribasic carboxylic acid such as nitrilotriacetic acid, citric acid, o-(carboxymethl) tartaric acid are mentioned. Further, mono-to tetra-sodium or potassium salt of 1,1,2,2-ethanetetracarboxylic acid, oxadisuccinic acid, and 2,5-dioxa-1,2,3,4,6-hexanetetracarboxylic acid are enumerated. Still further, aromatic tetrabasic carboxylic acids such as benzenetetracarboxylic acid and alicyclic tetrabasic carboxylic acids such as cyclohexanetetracarboxylic acid, 1,2,3,4,-cyclopentanetetracarboxylic acid, tetrahydrofurantetracarboxylic acid, etc. and alkali metal salts thereof, and hexabasic carboxylic acids such as 1,2,3,4,5,6,-hexanehexacarboxylic acid, benzenehexacarboxylic acid, 2,5-dioxa-1,1,3,4,6,6-hexanecarboxylic acid, 1,2,3,4,5,6,-cyclohexanehexacarboxylic acid, etc. and alkali metal salts thereof are enumerated. These polybasic carboxylic acids and their salts may be used alone or combining two kinds or more thereof.

Further, the above-mentioned oxymonocarboxylic acids and their salts of item (2) include gluconic acid, lactic acid, glycolic acid, hydracrylic acid, β-oxybutylic acid, and alkali metal (other than lithium) salts of the foregoing.

As for the imidosulfates of item (3), for example, imidobissulfates(neutral) such as $(NH_4SO_3)_2NH$, $(NaSO_3)_2NH.2H_2O$, and imidobissulfates (basic) such as $(NH_4SO_3)_2NNH_4.H_2O$, $(NaSO_3)_2NNa.H_2O$, $(NaSO_3)_2NNa.12\ H_2O$, etc. are enumerated. These imidosulfates have >NH bond in the molecule, and can be used in combination with various surfactant compositions, as new builders different from conventional ones in the chemical structure. In the present invention, these imdosulfates exhibit an effect as builder similarly to the case of the above-mentioned compounds of items (1) and (2), along with solubilization of metal soaps in water. Namely, the aqueous solutions thereof are neutral or weakly alkaline, and among them, trisodium salts are particularly superior in the alkali buffering property and also sufficient in the water-solubility; further, with respect to low toxicity which has recently become increasingly indispensable as the characteristic required for builders, acute and chronic toxicities, skin-stimulating property, toxicity to fishes, hemolytic property, concentrating property, etc. are extremely low. Further, these substances can be easily prepared from sulfur and ammonia as raw materials and their cost is cheap. Furthermore, they have a specific feature that the nitrogen content is particularly low in the case of the alkali metal salts, while the sulfur content is high. Thus, the practical value of metal soap compositions wherein these imidosulfates are used is notably high. Further, as for the polyphosphates of item (4), sodium, potassium and lithium salts of pyrophosphoric acid, tripolyphosphoric acid, tetrapolyphosphoric acid and hexametaphosphoric acid are enumerated, and generally sodium pyrophosphate, potassium pyrophosphate, sodium tripolyphosphate, sodium tetrapolyphosphate, sodium hexametaphosphate, etc. are used. It is suitable to use these polyphosphates alone or in combination.

As the examples of amines of item (5), ethylenediamine, diethylenetriamine, triethylentetramine, tetraethylenepentamine, pentaethylenehexamine, triethanolamine, monoethanolamine, etc, are enumerated.

As for the amino acids and salts thereof of item (6), glycine, taurine, glutamic acid, alanine, phenylalanine and salts of the foregoing are enumerated. Further as for the polyaminocarboxylic acids and salts thereof of item (7), nitrilotriacetic acid, 1,2-diaminocyclohexanetetraacetic acid, ethylene glycol bis (β-aminoethyl ether) tetraacetic acid, ethylenediaminetetraacetic acid, ethylenediaminetetrapropionic acid and salts of the foregoing are enumerated. As for the sulfur-containg carboxylic acids and salts thereof of item (8), xanthogenic acid and its salts are exemplified.

In the metal soap compositions of the present invention, it is preferable to mix the above-mentioned metal soap with one or a mixture or an aqueous solution of the above-mentioned various organic or inorganic chelating agents in a proportion in the range of 10 to 1/1000 part by weight based on one part by weight of the chelating agents, to thereby solubilize the metal soap in water, and a particularly preferable range of the proportion is 2 to 1/20 part by weight (at 20° to 30° C.).

The preparation of the metal soap composition of the present invention may be carried out by admixing a metal soap and a chelating agent and others dissolving them together on heating and then dissolving the resulting material in a suitable aqueous solvent such as water, etc. Alternatively the preparation may be carried out by dissolving a chelating agent in a solvent, thereafter adding a metal soap to the resulting solution and dissolving them together.

As for the amount of the metal soap compositions dissolved in the present invention, the concentration is usually in the rang of 0.1 to 80%, preferably 0.5 to 20% in aqueous solution; hence improvement to from about 3 to ∞ times the amount in the case of metal soap alone has been attained.

In this case, with regard to the solubility of metal soaps, the following tendency is generally observed:

Firstly as for metals, metal soaps of Li, Ca, Zn, Ni, etc. are generally easily soluble, but this tendency is not always fixed depending on the kinds of chelating agents, Further, as the temperature becomes higher, the solubility increases rapidly. As for the acid radicals, the shorter the chain is and the more the numbers of unsaturated bond and branch are, the easier the dissolution is. For example, solubility is as follows: ricinolic acid salt>oleic acid salt, and lauric acid salt>stearie acid salt.

The effect of the chelating agents upon the solubilization of metal soaps shows a tendency similar to the mutual relationship between general chelating agents and metals at the time of chelate formation, and such alkali metal salts as those of oxypolycarboxylic acids, aminocarboxylic acids, polycarboxylic acids, etc. are superior in the effect.

Next, in the metal soap compositions of the present invention, it is possible to further enhance the performances of the chelating agents (chelate effect and solubilizability), by further adding a conventional surfactant. The amount of such a surfactant and added has no particular limitation, but it is added usually in an amount in the range of 1 to 50% by weight, preferably 5 to 30% by weight based on the total weight of metal soap and chelating agent.

As such surfactant, the following are enumerated:

(1) As anionic surfactants for example, sodium alkylsulfate esters, sodium alkylbenzenesulfonates, sodium long chain α-olefin-sulfonates, alkylpolyoxyalkylene ether sulfate esters etc., as conventionally employed;

(2) As anionic surfactants for example, polyoxyethylene alkyl ethers, polyoxyethylene long chain fatty acid esters, polyoxyethylene-polyoxypropylene block copolymer, polyoxyethylene nonylphenyl ether, long chain fatty acid alkylolamide, etc.;

(3) As cationic surfactants, for example, tetraalkylammonium salts such as dodecyltrimethylammonium chloride, tetradecyldiethylolbenzylammonium nitrate, dioctyldimethylammonium chloride, N-alkylpyridinium halides such as N-dodecyl-2-propylpyridinium chloride, N-cetylpyridium bromide, alkylamine salts such as dodecylamine acetate salt, octadecylamine salt, etc.;

(4) As amphoteric surfactants, for example, alkylimidazolinium betaines such as 2-alkyl-N-carboxymethyl-N-hydroxyethylimidazolinium betaines, alkylglycine betains such as N-dodecyl-N, N-dimethylglycine betaine, alkyldiethylenetriamino acetic acid chloride, alkylaminoalkylsulfuric acids such as N-lauryl-N, N-dimethylaminopropylsulfuric acid, alkylaminoalkylsulfonic acids such as N-decyl-N, N-dimethylaminopropylsulfonic acid, N-dodecylaminomethylphosphoric acid, etc.

These surfactants may be employed alone or in admixture.

These surfactants are, if necessary, added to the compositions of the present invention in a proper amount, whereby precipitaion or white turbidity which occurs when the amount of chelating agents relative to that of metal soaps is somewhat insufficient can be prevented. Namely, use of surfactants in a proper amount makes it possible to avoid an occurrence of inferior dissolution state brought about depending on the hardness or temperature of water used. In the case where surfactants are used for such a purpose, those which have a long chain, a superior solubilizability and a low Krafft point are advantageous among the above-metioned surfactants.

Such metal soap compositions of the present invention are superior in the water-solubility, whereby it is possible to solubilize metal soaps in water as well as in oil without causing hydrolysis, and also exhibit properties as surfactant. Accordingly, it is possible to widely develop uses of metal soaps that had got problems with respect to solubility and stability and hence been restricted in their application fields.

In particular, the metal soap compositions of the present invention dissolved in water behave as if a single surfactant, and exhibit excellent surface active properties which are equal or superior to those of conventional surfactants. Namely, such aqueous solution exhibits not only general surface active properties such as wetting power, emulsifying power, dispersing power, etc., but also particular effect such as antimicrobial action, rust-preventive power, etc.

The function and effectiveness of the metal soap compositions of the present invention will be described below in more detail. Firstly as for the effect of metal soaps in the metal soap compositions, naturally the larger the amount there dissolved is, the greater the effect is but in some cases, even a small amount these of exhibits a function and effect suitable to particular purposes.

As for the concentration of metal soaps in the metal soap compositions, superior performances are, in many cases, exhibited when the concentration is in the range of 0.1 to 1.0% by weight, although this depends on the properties of surface active properties required. Particularly, metal soaps of $C_{10}$-$C_{18}$ carboxylic acids and in the case of long chains, those, having unsaturated bond, branched chain or hydroxyl group are advantageous.

When the meal soap compositions of the present invention are used, the surface tension of the aqueous solution thereof is reduced down to about 30 dyn/cm in a concentration of 0.2 to 1% and at a temperature of 20° to 30° C., but in the case of some metal soaps such as salts of lauric acid, the surface tention is reduced down to about 24 dyn/cm. Their wetting power is particularly excellent as compared with those of general surfactants, in the case of high concentration of the above-mentioned acids, and the wetting power in the case of salts of lauric acid is particularly good. Foaming is good in a great excess of chelating agents and their stability is also good in most cases. However, in the vicinity of the upper limit of the above-mentioned range of concentration, even when foaming occurs somewhat, foams are disappear in a short time; hence this is favorable in the case where low foaming property is required. Although emulsifing power and dispersing power vary depending upon combinations of metal soap with chelating agents, objectives to which the compositions are applied and other conditions, the above-mentioned properties are generally better when oleophilic metal soaps are used. Further, although rust-preventive power also considerably vary depending upon combinations of metal soaps with chelating agents and objective metals, the compositions are generally effective upon iron, copper, tinplate, etc. As for antimicrobial action, any of the compositions have considerably strong ones, and in particular, combinations of low toxic components are advantageous from the standpoint of practical uses.

As for surfactants, low toxic ones often required depending upon uses, but according to the compositions of the present invention, it is possible to readily provide low toxic ones. For example, compositions consisting of soaps of Ca, Mg, Al, etc. and salts of polycarboxylic acids such as cirtic acid, malic acid (both being food additives), etc., imidosulfates, etc. are extremely low toxic and very advantageous for uses. Magnesium soap of castor oil fatty acids is known to further reduce the toxicity of low toxic substances (Japanese Pat. No. 754,407 invented by the present inventor and Tsutsui); hence when this metal soap is used in the compositions of the present invention, great advantage is obtained.

Further, when usual surfactants are employed as mentioned above, the surfactants supplement the performances of chelating agents, and thereby improve the solubility of metal soaps and further enhance the above-mentioned various performances due to surface active properties.

The present invention will be more clearly understood with reference to Examples mentioned below.

Moreover, the respective tests in Examples were carried out according to the following methods:

(1) Surface tention: Measured by means of Du Noüy tensiometer at 22°-24° C.

(2) Wetting power: A sample solution (about 3 ml; depth 15 mm or deeper) is introduced into a beaker (10 ml); a test cloth (felt, 8×8 mm) is lightly placed on the surface of the solution by a pincette; and the seconds till the cloth sinks from the surface of the solution thereinto are measured. The measurement temperature 22°-24° C. The evaluation standards are as follows;

| Evaluation | Time (second) |
|---|---|
| 5 | ~3.0 |
| 4 | 3.1~20.0 |
| 3 | 20.1~50.0 |

-continued

| Evaluation | Time (second) |
|---|---|
| 2 | 50.1 ~ 200.0 |
| 1 | 200.1 ~ |

(3) Foaming power: A sample solution (2.0 g) is introduced into a test tube equipped with a stopper (12×65 mm); the tube is vertically shaked at 25 cm/20 times/10 seconds and allowed to stand at room temperature; and just thereafter and after 30 minutes, the heights of foam are measured. Average values were obtained. Stability of foam was expressed by $$\frac{\text{Height of foam after 30 minutes}}{\text{Height of foam just thereafter}} \times 100\%$$

(4) Emulsifying power: A sample (0.5 ml) and an oil (0.5 ml) (height: 1.5 cm) are introduced into a test tube equipped with a stopper (8×50 mm); the tube is stood on a hot bath, allowed to stand for 5 minutes, thereafter stoppered, vertically shaked at 25 cm/20 times/10 seconds, and allowed to stand on the hot bath at 90° C. for 30 minutes; the height and visible turbidity of the resulting emulsified layer are measured; they are evaluated, respectively; and average values are calculated between these measured values and those obtained by still standing at 20°-24° C. for 24 hours.

Evaluation standards are as follows;

| Evaluation | Height of emulsified layer (cm) | Turbidity |
|---|---|---|
| 5 | 1.5 ~ | very thick |
| 4 | 1.0 ~ 1.4 | considerably thick |
| 3 | 0.5 ~ 0.9 | medium |
| 2 | 0.1 ~ 0.4 | thin |
| 1 | 0 | transparent |

In addition, cotton seed oil (required HLB: 10), liquid paraffin (requied HLB: 12) and dimethyl phthalate (required HLB: 15) were imployed as the above oil.

(5) Dispersing power: A sample (1 ml) and carbon black (about 3 mg) are introduced into a test tube (same as that in the item (2)); the tube is stopped and vertically shaked at 25 cm/20 times/10 seconds; and after 5 hours, the height and turbidity of the resulting dispersed layer are measured and evaluated, respectively and the average values are calculated.

Temperature: 22° ~ 24° C.

Evaluation standards are as folloes:

| Evaluation | Height h/(cm) | Turbidity |
|---|---|---|
| 5 | 2.8 ~ 3.0 | very thick |
| 4 | 2.0 ~ 2.7 | considerably thick |
| 3 | 1.0 ~ 1.9 | midium |
| 2 | 0.1 ~ 0.9 | thin |
| 1 | 0 | transparent |

(6) Rust-preventive power: A sample aqueous solution (about 4 ml) is introduced into a test tube equipped with a stopper (same as that in the item (3)); a test metal piece (a wire of about 20 mm or a metal plate of 4×20×0.8 ~ 1.6 mm) is immersed in the solution; and after lapse of 24 hours on a hot bath at 90° C., the change of the metal piece is observed with naked eyes.

Evaluation standards are as follows:

| Evaluation | Surface condition |
|---|---|
| 5 | No change |
| 4 | Luster is slightly reduced; rust are formed at only a small part; solution is slightly turbid. |
| 3 | Changes described above in evaluation 4 are somewhat enlarged. |
| 2 | Considerably changed: rust is formed on about ½ of the surface area |
| 1 | Greatly changed; total surface is coated by rust; solution is notably discolored or precipitate is formed. |

Metal pieces employed for the above corrosion test are shown in Table 1.

TABLE 1

| Metal | Name | Use | Test No. | JIS No. |
|---|---|---|---|---|
| Aluminum | High-strength aluminum alloy | | | JIS H 4000 A2024P |
| Steel (A) | Mill shape for general structure | For antifreeze | JIS K2234 | JIS G 3101 SS-41 |
| Steel (B) | Cold-rolled steel | | JIS Z0236 | JIS G 3141 SPCCB |
| Copper | | For antifreeze | K2234 | JIS H 3101 TCUP1 |
| Brass | | For antifreeze | K2234 | JIS H 3201 BISP3 |
| Phospher bronze | (Wire) | | | |
| Zinc plate | | | | |
| Tin plate | | | | |
| Solder | (for soldering) | | | |

(7) Antimicrobial action

A sample aqueous solution (3 g) of various concentration, and agar medium (Kyokuto standard culture medium: yeast extract-peptone, glucose, agar) (80 mg) are introduced into a test tube equipped with a stopper (12×65 mm); dissolved on the heating at about 80° C.; slanted and cooled; after solidification, allowed to stand outdoor for about one hour; and lightly stoppered and allowed to stand at 38° C. for 1 to 7 days; and growth conditions of fungi (infections microbes in air, yeast, molds) are observed.

EXAMPLE 1

Various properties of an aqueous solution obtained by dissolving calcium salt of castor oil fatty acids in tetrasodium ethylenediaminetetraacetate were tested. The results are shown in Table 2. Test results obtained with aqueous solutions of the respective components alone are also shown in the same Table.

From these results it can be seen that the mixture system of the above-mentioned two components exhibits its superior surface active properties. (As for rust-preventive power a part of the results is superior even with the soap alone, but it is difficult to use the soap in practical due to its insoluble state dispersion)

TABLE 2

| | | | | Surface active property | | | | | | | | | | | | | | | | | |
|---|---|---|---|---|---|---|---|---|---|---|---|---|---|---|---|---|---|---|---|---|---|
| | | | | | | | | | Emulsifying power | | | | | | | | | | | | |
| | | | | | | | | | Cotton seed oil | | | | Liquid paraffin | | | | Dimethyl phthalate | | | | |
| Experiment No. | Sample | wt. % | Solution state | Surface tension (dyn/cm) | Wetting power (sec) Felt | Foaming power Foaming (mm) A | Foaming power Foaming (mm) A' | Foaming power Stability % | Height A | Height B | Turbidity A | Turbidity B | Height A | Height B | Turbidity A | Turbidity B | Height A | Height B | Turbidity A | Turbidity B |
| 1 | CaCO | 0.5 | White dispersion (slight dissolution) | 46.0 | >200 | 0 | 0 | — | 5 | 4 | 4 | 2 | 4 | 3 | 2 | 2 | 5 | 2 | 4 | 2 |
| | | | | | | | | | | (3.8) | | | | (2.8) | | | | (3.3) | | |
| 2 | EDTA | 0.8 | Colorless transparent | 58.9 | >200 | 0 | 0 | — | 5 | 3 | 4 | 2 | 5 | 1 | 3 | 1 | 5 | 1 | 2 | 1 |
| | | | | | | | | | | (3.5) | | | | (2.5) | | | | (2.3) | | |
| 3 | CaCO—EDTA | 0.5-0.8 | Nearly colorless transparent | 39.3 | 28.7 | 17 | 9 | 53 | 5 | 5 | 5 | 4 | 5 | 3 | 4 | 4 | 5 | 4 | 4 | 3 |
| | | | | | | | | | | (4.5) | | | | (4.0) | | | | (4.0) | | |

| Surface active property | | | | | | | | | | | | | | | | | | | | |
|---|---|---|---|---|---|---|---|---|---|---|---|---|---|---|---|---|---|---|---|---|
| Dispersing power | | | | | | | | | | | | Rust preventive power | | | | | | | | |
| Carbon black | | | | Manganese dioxide | | | | Titanium dioxide | | | | | Steel | | | | Phospher | Zinc | Tin | |
| Height A' | Height B | Turbidity A' | Turbidity B | Height A' | Height B | Turbidity A' | Turbidity B | Height A' | Height B | Trubidity A' | Trubidity B | Aluminum | A | B | Brass | Copper | bronze | plate | plate | Solder |
| 1 | 1 | 1 | 1 | 5 | 1 | 2 | 1 | 5 | 1 | 4 | 1 | 4 | 4 | 3 | 2 | 4 | 5 | 1 | 3 | 5 |
| | (1) | | | | | (2.3) | | | | (2.8) | | | | | | (3.1) | | | | |
| 1 | 1 | 1 | 1 | 5 | 1 | 3 | 1 | 5 | 1 | 2 | 1 | 1 | 3 | 3 | 1 | 1 | 1 | 3 | 5 | 2 |
| | (1) | | | | | (2.5) | | | | (2.3) | | | | | | (2.0) | | | | |
| 5 | 4 | 5 | 3 | 5 | 1 | 3 | 1 | 5 | 1 | 5 | 1 | 3 | 4 | 5 | 4 | 1 | 1 | 2 | 5 | 3 |
| | (4.3) | | | | | (2.5) | | | | (3.0) | | | | | | (2.8) | | | | |

Note:
A: 30 minutes
B: after 24 hours
A': just after the start of test

Evaluation of emulsifying power, dispersing power and rust-preventive power: according to 5-grade evalation method. (This applies to the following Examples.)

EXAMPLE 2

With aqueous solution of 6 kinds of compositions consisting of metal soaps and chelating agents shown in the following Table 3, various properties indicating surface active properties were measured in the same manner as in Example 1. At the same time, with 3 representative surfactants, surface active properties were measured in the same manner. The name of sample, blending ratio, etc. of the respective experimental examples are shown in Table 3, and the measured results are shown in Table 4.

TABLE 3

| | Experiment No. | Metal soap or surfactant | Abbreviation symbol | Chelatining agent | abbreviation symbol | Amount blended | Note |
|---|---|---|---|---|---|---|---|
| Present invention | 1 | Mg salt castor oil fatty acids | MgCO | Na citrate | SCit | 0.5:0.8 | |
| | 2 | Mg salt castor oil fatty acids | MgCO | Na tartrate | STart | 0.5:6.5 | |
| | 3 | Trialuminum octoate* | $AlOct_3$ | Na pyrophosphate | SPP | 0.5:1.25 | |
| | 4 | Co laurate | $CoL_2$ | Na ethylenediaminetetraacetate | EDTA | 0.2:2.0 | |
| | 5 | Li laurate | LiL | Trisodium imidobissulfate | TSIS | 0.2:1.6 | |
| | 6 | Trialuminum octoate* | $AlOct_3$ | Trisodium imidobissulfate | TSIS | 0.1:3.0 | Slightly opaque |
| Comparative | 7 | Na dodecylsulfate | SDS | | | 0.5 | |
| | 8 | Na straight chain-alkylbenzene-sulfonate | LAS | | | 0.5 | |

TABLE 3-continued

| | Experiment No. | Metal soap or surfactant | Abbreviation symbol | Chelatining agent | abbreviation symbol | Amount blended | Note |
|---|---|---|---|---|---|---|---|
| example | | | | | | | |
| | 9 | Polyoxyethylene (20mols) nonylphenyl ether | NP-20 | | | 0.5 | |

*2-ethylhexoate

TABLE 4

| Surface active property | | | | Experiment No. 1 | 2 | 3 | 4 | 5 | 6 | 7 | 8 | 9 |
|---|---|---|---|---|---|---|---|---|---|---|---|---|
| Surface tention (dyn/cm) | | | | 36.6 | 34.9 | 52.8 | 37.6 | 38.2 | 49.1 | 38.2 | 34.7 | 41,0 |
| Wetting power (sec) | Felt | | | 5.6 | 2.5 | >200 | 16.2 | >200 | >200 | 60.0 | 5.5 | >200 |
| Foaming power | Foaming (mm) | | A | 18 | 16 | 0 | 15 | 25 | 0 | 20 | 24 | 20 |
| | Foaming (mm) | | A' | 4 | 3 | 0 | 6 | 6 | 0 | 11 | 21 | 14 |
| | Stability (%) | | | 22 | 19 | 0 | 40 | 24 | 0 | 55 | 88 | 70 |
| Emulsifying power | Cotton seed oil | Height | A | 5 | 5 | 5 | 5 | 5 | 5 | 5 | 5 | 5 |
| | | | B | 5 (4.3) | 3 (3.3) | 4 (4.0) | 5 (4.8) | 5 (5.0) | 4 (3.8) | 5 (4.0) | 3 (4.0) | 1 (2.3) |
| | | Turbidity | A | 4 | 3 | 4 | 5 | 5 | 4 | 4 | 5 | 2 |
| | | | B | 3 | 2 | 3 | 4 | 5 | 2 | 2 | 3 | 1 |
| | Liquid paraffin | Height | A | 5 | 5 | 5 | 5 | 5 | 5 | 5 | 5 | 5 |
| | | | B | 2 | 2 | 1 | 4 | 4 | 1 | 1 | 2 | 1 |
| | | Turbidity | A | 2 (2.8) | 2 (2.8) | 2 (2.3) | 3 (3.5) | 3 (3.5) | 2 (2.3) | 2 (2.3) | 3 (3.0) | 2 (2.3) |
| | | | B | 2 | 2 | 1 | 2 | 2 | 1 | 1 | 2 | 1 |
| | Dimethyl phthalate | Height | A | 5 | 5 | 5 | 5 | 5 | 5 | 5 | 5 | 5 |
| | | | B | 4 (3.3) | 1 (2.8) | 1 (2.5) | 4 (3.8) | 1 (2.8) | 1 (2.3) | 3 (3.3) | 3 (3.5) | 4 (3.8) |
| | | Turbidity | A | 4 | 4 | 3 | 4 | 4 | 2 | 3 | 4 | 4 |
| | | | B | 2 | 1 | 1 | 2 | 1 | 1 | 2 | 2 | 2 |
| Dispersing power | Carbon black | Height | A' | 5 | 5 | 1 | 5 | 5 | 1 | 5 | 5 | 5 |
| | | | B | 4 (4.5) | 1 (3.0) | 1 (1.0) | 4 (4.3) | 4 (4.3) | 1 (1.0) | 5 (4.0) | 4 (4.5) | 4 (3.8) |
| | | Turbidity | A' | 5 | 5 | 1 | 5 | 5 | 1 | 4 | 5 | 4 |
| | | | B | 4 | 1 | 1 | 3 | 3 | 1 | 2 | 4 | 2 |
| | Managnese dioxide | Height | A' | 5 | 5 | 5 | 5 | 5 | 1 | 5 | 5 | 5 |
| | | | B | 5 (4.3) | 4 (3.8) | 1 (2.3) | 1 (2.3) | 4 (3.5) | 1 (1.0) | 1 (2.5) | 3 (3.8) | 1 (2.8) |
| | | Turbidity | A' | 4 | 4 | 2 | 2 | 3 | 1 | 3 | 5 | 4 |
| | | | B | 3 | 2 | 1 | 1 | 2 | 1 | 1 | 2 | 1 |
| | Titanium dioxide | Height | A' | 5 | 5 | 5 | 5 | 5 | 5 | 5 | 5 | 5 |
| | | | B | 1 (3.0) | 1 (3.0) | 1 (2.3) | 1 (3.0) | 1 (3.0) | 1 (2.3) | 4 (4.5) | 4 (4.5) | 4 (4.5) |
| | | Turbidity | A' | 5 | 5 | 2 | 5 | 5 | 2 | 5 | 5 | 5 |
| | | | B | 1 | 1 | 1 | 1 | 1 | 1 | 4 | 4 | 4 |
| Rust-preventive power | Aluminum | | | 2 | 3 | 3 | 2 | 5 | 1 | 3 | 3 | 4 |
| | Steel (A) | | | 5 | 4 | 5 | 5 | 5 | 1 | 4 | 3 | 1 |
| | Steel (B) | | | 3 | 3 | 5 | 5 | 5 | 2 | 3 | 3 | 2 |
| | Brass | | | 4 | 3 | 5 | 4 | 4 | 2 | 3 | 5 | 4 |
| | Copper | | | 3 (3.4) | 3 (3.3) | 5 (4.2) | 5 (3.3) | 3 (4.1) | 2 (1.6) | 3 (3.3) | 4 (3.3) | 5 (3.3) |
| | Phosper bronze | | | 3 | 5 | 4 | 5 | 5 | 1 | 5 | 4 | 4 |
| | Zinc plate | | | 3 | 3 | 2 | 3 | 3 | 2 | 3 | 2 | 2 |
| | Tin plate | | | 4 | 3 | 4 | 4 | 4 | 2 | 3 | 3 | 4 |
| | Solder | | | 4 | 3 | 5 | 3 | 3 | 1 | 3 | 3 | 4 |

EXAMPLE 3

A composition obtained by dissolving 8 parts by weight of sodium citrate (S Cit) in 5 parts by weight of magnesium salt of castor oil fatty acids (MgCO) was made up into aqueous solutions having difinite concentrations, and their antimicrobial action were tested. For comparison, the same test was carried out only with sodiumcitrate. The results are shown in Table 5.

TABLE 5

| | Test No. No. 1 | | | | No. 2 | | |
|---|---|---|---|---|---|---|---|
| | Sample MgCo-SCit | | | | SCit | | |
| Concentration | Day 1 | 3 | 5 | 7 | 1 | 3 | 5 |
| 1.0 (wt %) | — | — | — | — | ⊥ | + | ++ |

TABLE 5-continued

| | Test No. No. 1 | | | | No. 2 | | |
|---|---|---|---|---|---|---|---|
| | Sample MgCo-SCit | | | | SCit | | |
| Concentration | Day 1 | 3 | 5 | 7 | 1 | 3 | 5 |
| 0.5 | — | — | — | — | — | + | ++ |
| 0.25 | — | — | — | — | — | + | +++ |
| 0.10 | — | — | — | — | — | + | +++ |
| 0.05 | — | — | ⊖ | — | — | + | +++ |
| 0.01 | — | — | ⊥ | + | — | + | +++ |
| 0.005 | — | ⊖ | + | + | | | |
| 0.001 | + | +++ | +++ | +++ | | | |
| Blank | + | ++ | +++ | — | | | |
| Minimum inhabitory concentration | | | 0.005 | | | >1.0 | |

TABLE 5-continued

| | Test No. | | | | | | |
|---|---|---|---|---|---|---|---|
| | No. 1 | | | | No. 2 | | |
| | Sample | | | | | | |
| | MgCo-SCit | | | | SCit | | |
| Concent- | Day | | | | | | |
| ration | 1 | 3 | 5 | 7 | 1 | 3 | 5 |
| (3 days) | | | | | | | |

(Note)
—: No colony develops
⊖: Ditto, minimum inhibitory concentration
⊥: Slightly develops
+: Medium in development
+ +: Considerably develops
+ + +: Develops on the total surface From the results of Examples 2 and 3, it can be seen that the compositions of the present invention exhibit an effect which is equal or superior to those of surfactants. Moreover, in Example 2, any case of chelating agents alone scarcely exhibited the above-mentioned surface active properties.

EXAMPLE 4

A composition solution consisting of calcium salt of castor oil fatty acids (CaCO), tetrasodium ethylenediaminetetraacetate (EDTA) and polyoxyethylene nonylphenyl ether (NP-12) as a surfactant was prepared and their surfase active properties were examined. The results are shown in Table 6 together with those of composition in which no NP-12 is added for comparison. Experiment No. 2 is an example where NP-12 of Experiment No. 1 is not added. From the results of these two experiments, it can be seen that even when metal soap and chelating agent are not completely dissolved together, it is possible to solubilize the both together by adding a surfactant. Further, an example shown as reference in Table 6 is that of Experiment No. 3 of Example 1. By comparing the results of Experiment No. 1, Experiment No. 2 and the reference, it can be seen that when a surfactant is added, it is possible to reduce the amount of somewhat expensive EDTA used and more clarify and more stabilize the solution state (i.e. lowering Krafft point), to thereby make the use of product at low temperature possible and improve its dispersing power and rust-preventive power.

TABLE 6

| | | | | Experiment No. | | | |
|---|---|---|---|---|---|---|---|
| | | | | 1 | | 2 | Reference |
| | | | | Sample | | | |
| | | | | CaCO-EDTA(4)-NP12 0.5-0.5-0.3 | | CaCO-EDTA(4) 0.5-0.5 | CaCO-EDTA(4) 0.5-0.8 |
| | | | | Solution state | | | |
| Surface active property | | | | Colorless transparent | | Partly insoluble (precipitation) | Nearly colorless, transparent |
| Surface tension (dyn/cm) | | | | 38.0 | | | |
| Wetting power (sec) | Felt | | | 22.2 | | | |
| Foaming power | Foaming (mm) A' | | | 6 | | | |
| | Foaming (mm) A | | | 2 | | Impossible to measure | The same as those of Experiment 3 of Example 1. |
| | Stability (%) | | | 33 | | | |
| Emulsifying power | Cotton seed oil | Height | A | | | | |
| | | | B | 3 | (4.3) | | |
| | | Turbidity | A | 5 | | | |
| | | | B | 4 | | | |
| | Liquid paraffin | Height | A | 5 | | | |
| | | | B | 5 | (4.0) | | |
| | | Turbidity | A | 3 | | | |
| | | | B | 3 | | | |
| | Dimethyl phthalate | Height | A | 5 | | | |
| | | | B | 2 | (3.0) | | |
| | | Turbidity | A | 3 | | | |
| | | | B | 2 | | | |
| Dispersing power | Carbon black | Height | A' | 5 | | | |
| | | | B | 4 | | | |
| | | Turbidity | A' | 5 | (4.5) | | |
| | | | B | 4 | | | |
| | Manganese dioxide | Height | A' | 5 | | | |
| | | | B | 1 | | | |
| | | Turbidity | A' | 5 | (3.0) | | |
| | | | B | 1 | | | |
| | Titanium dioxide | Height | A' | 5 | | | |
| | | | B | 1 | (3.0) | | |
| | | Turbidity | A' | 5 | | | |
| | | | B | 1 | | | |
| Rust-preventive power | Aluminum | | | 4 | | | |
| | Steel (A) | | | 5 | | | |
| | Steel (B) | | | 5 | | | |
| | Brass | | | 4 | | | |
| | Copper | | | 4 | (3.7) | | |
| | Phosper bronze | | | 5 | | | |

TABLE 6-continued

| | | Experiment No. | | |
|---|---|---|---|---|
| | | 1 | 2 | Reference |
| | | Sample | | |
| | | CaCO-EDTA(4)-NP12 0.5-0.5-0.3 | CaCO-EDTA(4) 0.5-0.5 | CaCO-EDTA(4) 0.5-0.8 |
| | | Solution state | | |
| Surface active property | | Colorless transparent | Partly insoluble (precipitation) | Nearly colorless, transparent |
| | Zinc plate | 3 | | |
| | Tin plate | 3 | | |
| | Solder | 4 | | |

Having described a specific embodiment of our bearing, it is believed obvious that modification and variation of our invention is possible in light of the above teachings.

What is claimed is:

1. A water-soluble metal soap composition which consists essentialy of a metal soap selected from the group consisting of lithium stearate, calcium ricinoleate, lithium laurate, cobalt laurate, aluminum monooleate, stannous caprate, copper naphthenate, zinc linoleate, zirconium rosinate, vanadium caprylate, tungsten capronate, manganese ricinoleate, cobalt myristate, calcium salt of castor oil fatty acid, magnesium salt of castor oil fatty acid, and trialuminum octoate, and a chelating agent, said metal soap being present in said composition in an amount of 10 to 1/1000 part by weight based on one part of said chelating agent.

2. A water-soluble metal soap composition which consists essentially of a metal soap selected from the group consisting of lithium stearate, calcium ricinoleate, lithium laurate, cobalt laurate, aluminum monooleate, stannous caprate, copper naphthenate, zinc linoleate, zirconium rosinate, vandium caprylate, tungsten capronate, manganese ricinoleate, cobalt myristate, calcium salt of castor oil fatty acid, magnesium salt of castor oil fatty acid, and trialuminum octoate, a chelating agent and up to 50% by weight based on the total amount of said metal soap and said chelating agent of a surfactant, said metal soap being present in said composition in an amount of 10 to 1/1000 part by weight based on one part of said chelating agent.

3. An aqueous solution of the water-soluble metal soap composition of claims 1 or 2, said metal soap composition being present in an amount of 0.2-20% by weight, with the substantial balance being water.

4. The aqueous solution of the water-soluble metal soap composition of claims 1 or 2 wherein the chelating agent is selected from the group consisting of polybasic carboxylic acids and salts thereof, oxymonocarboxylic acids and alkali metal (other than lithium) salts thereof, imidosulfates, polyphosphates, amines, amino acids and salts thereof, polyamino carboxylic acid salts, and sulfur-containing carboxylic acid salts.

5. The aqueous solution of the water-soluble metal soap composition of claim 2 wherein the surfactant is selected from the group consisting of anionic surfactants, nonionic surfactants, cationic surfactants and amphoteric surfactants.

6. The aqueous solution of the water-soluble metal soap composition of claim 2 wherein the metal soap is the calcium salt of castor oil fatty acids, the chelating agent is tetrasodium ethylenediamine-tetraacetate and the surfactant is polyoxyethylene nonylphenyl ether, said metal soap-chelating agent-surfactant being present in an amount of 0.5-0.5-0.3 parts by weight, respectively.

* * * * *